United States Patent [19]

Mallouk et al.

[11] Patent Number: 4,863,974

[45] Date of Patent: Sep. 5, 1989

[54] BONE GROWTH MATRIX AND PROCESS FOR MAKING IT

[75] Inventors: Robert S. Mallouk, Chadds Ford, Pa.; William P. Mortimer, Jr., New Castle, Del.

[73] Assignee: W. L. Gore & Associates, Inc., Newark, Del.

[21] Appl. No.: 227,935

[22] Filed: Aug. 3, 1988

[51] Int. Cl.⁴ ............................................. C08J 9/24
[52] U.S. Cl. .................................. 521/85; 433/201.1; 433/212.1; 424/78; 521/145; 521/919; 523/115; 523/451; 524/417; 623/10; 623/16
[58] Field of Search .................. 521/85, 145; 523/113, 523/115; 424/78

[56] References Cited

U.S. PATENT DOCUMENTS

| | | | |
|---|---|---|---|
| 3,443,261 | 5/1969 | Battista | 3/1 |
| 4,256,845 | 3/1981 | Morris et al. | 521/61 |
| 4,373,217 | 2/1983 | Draenert | 3/1.9 |
| 4,497,075 | 2/1985 | Niwa | 3/1.9 |
| 4,518,430 | 5/1985 | Brown | 3/1.9 |
| 4,548,959 | 10/1985 | Nagai et al. | 523/115 |
| 4,576,608 | 3/1986 | Homsy | 3/1.9 |

*Primary Examiner*—Morton Foelak
*Attorney, Agent, or Firm*—Gary A. Samuels

[57] ABSTRACT

The present invention provides for a bone growth material for filling in defects or hollow portions of bones to be ingrown by and coalesce with bone tissues wherein the bone growth material is comprised of expanded PTFE and calcium phosphate.

4 Claims, 1 Drawing Sheet

Scale=500X

|←—— 50 MICRONS

Scale=100X

|←—— 50 MICRONS

BONE GROWTH MATRIX AND PROCESS FOR MAKING IT

FIELD OF THE INVENTION

The present invention relates to expanded polytetrafluoroethylene (hereafter expanded PTFE) containing an inorganic filler. The filled expanded PTFE is used to place into defects or hollow portions of bones in a living body to facilitate formation of new bone tissue in the voids in the expanded PTFE.

BACKGROUND OF THE INVENTION

In the dental field, the oral-maxillo facial field, the orthopedic field or other surgical fields, defects and hollow portions of bones can be formed during highly complicated fractures or removal operations. To fill in these defects, prior art techniques included taking pieces from flank bones or other bones of the patient and filling in the injured portion of bone with these bone fragments. This method is not desirable as the patient suffers pain since bone tissue other than the injured portion is taken out for use. It also requires an extra operation. In addition, a sufficient amount of autoplastic bone cannot always be taken from the patient's body.

Various metals and plastic materials have also been used as substitute materials for bones in the human body. However, metals are difficult to fit to irregular cavities and, even when snugly fitted, cause stress and concomitant trauma to overlying soft tissue or frequently cause the surrounding bone to resorb, thus enlarging the cavity.

Fully polymerized plastics are also difficult to rapidly cut and shape to fit irregular cavities. A commonly accepted approach therefore has been to use a methyl methacrylate/polymethylmethacrylate dough or cement which readily comforms to irregular cavities and polymerizes in place. However, the polymer is relatively brittle and hard and unsuitable for filling cavities which will experience stress. Moreover permanent adhesion to the surrounding bone is rarely achieved.

Both metal and polymeric implant systems have been devised which provide for some measure of void space for ingrowth or attachment to surrounding bone. However, the void space provided is such that ingrowth is limited and a relatively sharp transition remains between the implant and the surrounding bone. This results in stress concentrations which can result in bone resorption and loosening of the implant or trauma to overlying soft tissue.

Biomaterials of ceramics made of single crystalline or polycrystalline alumina ($Al_2O_3$), sintered calcium tertiary phosphate ($Ca_3(PO_4)_2$) and sintered hydroxyapatite ($Ca_5(PO_4)_3OH$) have also been used as substitute materials. These materials are not desirable however, as they are hard and brittle.

U.S. Pat. No. 3,443,261 teaches a homogeneous mixture of a water-insoluble, microcrystalline ionizable salt of collagen, calcium phosphate and water. Fibers such as polyesters, nylon, polytetrafluoroethylene (PTFE), polyolefins, and polycarbonates are added to the calcium phosphate mixture to increase the hardness. Calcium phosphates included dicalcium phosphate, tricalcium phosphate, octacalcium phosphate, hydroxyapatite, carbonate apatite, chlorapatite, fluoroapatite and mixtures thereof. The relative hardness, flexibility, plasticity, and rigidity were dependent on the relative proportions of the organic and inorganic constituents and structural morphology.

U.S. Pat. No. 4,373,217 teaches an implantation material comprising a polymeric base of an acrylate, a polymethacrylate and a methacrylate or a mixture thereof, and 5–35% by weight of resorbable tricalcium phosphate of a particle size of 50–300 um and an available pore volume of less than 0.1 ml/g.

U.S. Pat. No. 4,518,430 teaches an implantation composition comprising tetracalcium phosphate and at least one other sparingly soluble calcium phosphate solid in equilibrium with a dilute aqueous solution.

U.S. Pat. No. 4,497,075 teaches the use of powders of a calcium phosphate compound having apatite crystalline structures or apatite calcium phosphate compounds which include hydroxyapatite having the general formula $Ca_m(PO_4)_nOH$ ($1.33 \leq m/n \leq 1.95$). The crystallite size of the apatite calcium phosphate compound is described to be 400 A° or larger, while the crystal grain size of the same compound should be 3 um or smaller.

The implantable materials comprised of calcium phosphates and derivatives thereof as described above have several drawbacks in that none provide for resilience and strength. In addition, they lack a high void volume and/or large enough void channels to provide for potential living tissue ingrowth. Also, tricalcium phosphate or hydroxyapatite powders and granules are deficient in shaping and in maintaining a given shape.

SUMMARY OF THE INVENTION

A bone growth matrix for filling in defects or hollow portions of bones to coalesce with bone tissues wherein said bone growth matrix is comprised of between 1.5 to 12% by volume expanded polytetrafluoroethylene and between 2.5 to 18% by volume calcium phosphate, in which said matrix is resilient and in which the remaining volume contains voids of a size capable of allowing for tissue ingrowth.

DESCRIPTION OF THE INVENTION

Figure 1:
FIGS. 1 and 2 are microphotographs of structures of this invention.
Figure 2:
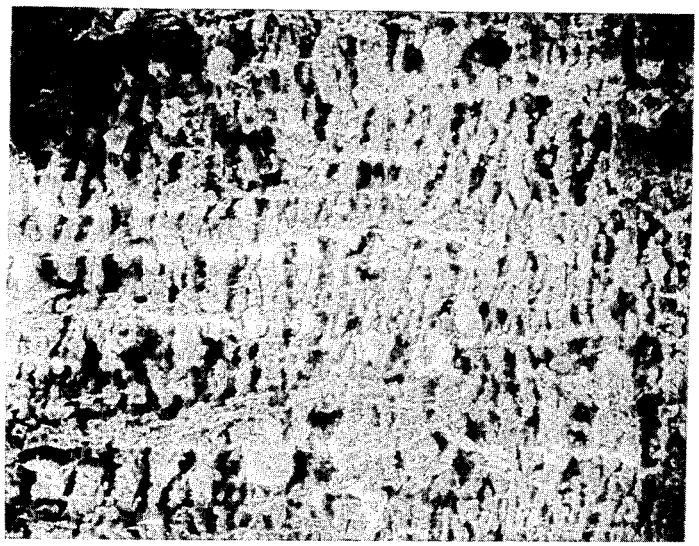

This invention comprises a resilient bulk material comprising calcium phosphate and expanded PTFE (expanded PTFE) having voids into which both hard and/or soft tissue may grow depending on the method of use in the human body. The voids in the expanded PTFE are interconnected channels formed by expansion of PTFE carried out according to U.S. Pat. No. 3,953,566. The expanded PTFE has a void volume of greater then 70% and preferably between 80 and 93%. The voids are interconnected channels large enough to permit capillary and tissue ingrowth. The expanded PTFE acts to hold the calcium phosphate particles together so that the combination can easily be shaped to build up bone structure yet retain a measure of physical integrity, compressive strength, and resilience.

The combination of calcium phosphate and expanded PTFE is an improvement over known calcium phosphate composites because the combination provides a significant volume of void space and channels which permit potential bone ingrowth.

The material of the invention can be used to permit bone ingrowth in a defined space. The material allows for good attachment to adjacent hard bone tissue as a result of such ingrowth. It is important to provide a tough resilient structure, particularly in dental and maxillo-facial applications.

The inventive bone growth material is easy to handle and is adaptable to many different shapes and sizes. The surgeon using the material may easily cut it to size and manipulate it to fit the space to be filled and maintain it for a time sufficient for bone ingrowth to occur.

The preferred form of calcium phosphate is calcium triphosphate of the general formula $Ca_5(PO_4)_3OH$. It can be either the resorbable type or nonresorbable type, such as hydroxyapatite.

The compositions of the invention are prepared by mixing a slurry of calcium phosphate particulate and a dispersion of polytetrafluoroethylene (PTFE) that had been prepared by the dispersion method for polymerizing tetrafluoroethylene. As the mixing is conducted, the PTFE and calcium phosphate co-coagulate and form an intermixed material. This material is dried, the usual type lubricant added, a pellet formed and the material expanded, all as taught in U.S. Pat. No. 3,953,566. The resulting material forms one composition of the invention. The calcium phosphate particulate is dispersed throughout the nodes in the expanded PTFE matrix.

The resulting material can be sintered and is then ready for use as bone supplement.

The material comprises mostly nodes and fibrils of expanded PTFE with the calcium phosphate particles interspersed throughout and on the nodes. The channels, or space between nodes, appear to be in the 50-200 micron range. Referring to the figures, the light portion of the microphotographs are the calcium phosphate particles collected around the nodes. The darker areas are the channels or voids. The fibrils can be seen as thin lines.

The material is resilient and retains physical integrity on deformation under load. It can be cut and shaped to form various shapes without losing its physical integrity.

EXAMPLE 1

The tricalcium phosphate used was composed of aggregates of particles about 0.2-20 microns in diameter.

A slurry of 643 g. precipitated tribasic calcium phosphate $(Ca_5(OH)(PO_4)3)$ obtained from Baker Chemical Co. and 10,075 cc of de-ionized water was prepared in a 19 l container. The container, 35 cm deep and 11 cm in diameter, had two 2.5 cm baffles opposite each other. There were two 9.5 cm three leaf propellers on the mixing shaft. The bottom propeller was set 2 cm from the bottom of the vessel and the second propeller was 9 cm above it. While the slurry agitated at 225 rpm, a 6.0% solids PTFE dispersion was rapidly poured into the mixing vessel. The PTFE dispersion was Fluon AD-059 obtained from ICI Americas Co. Within 30 seconds co-coagulation was complete. After 10 minutes the coagulum had settled to the bottom of the mixing vessel and the water was clear.

The coagulum was dried at 160° C. in a convection oven. The material dried in small cracked cakes approximately 2 cm thick was then chilled to −10° C. The chilled cake was hand ground using a tight circular motion and minimal downward force through a 0.635 cm mesh stainless steel screen. Then 0.573 cc of mineral spirits lubricant was added per gram of powder. The mixture was chilled to −10° C., again passed though a 0.635 cm mesh screen, tumbled for 10 minutes, then allowed to sit at 18° C. for 8 hours and retumbled for 10 minutes.

A pellet was formed by filling a 2.54 cm diameter cylinder with this lubricated powder and pressing at 20 psi. The pellet was loaded into a 2.54 cm ram extruder fitted with a 0.635 cm beading die. The extruder ram was advanced at 2.59 cm/min until the beading began to extrude. The ram was retracted and the ram speed was adjusted to 8.9 cm/min to extrude the bead.

The mineral spirits lubricant was evaporated in a convection oven for 18 hours at 100° C. followed by two hours at 230° C.

5.08 cm lengths of beading were heated to 260° C. for 2 minutes and expanded 300% (i.e. 4:1) at a rate of 38.1 cm/sec. (15 inches per sec.).

The expanded beading was cooled to room temperature then allowed to relax unrestrained for 30 minutes. Then the relaxed expanded beading was pulled taut and sintered in a convection oven for 3 minutes at 350° C. The residual elongation was determined to be 265% by comparing the weights per unit length of the expanded sintered beading with that of the unexpanded precursor. The bulk density of the expanded, sintered beading, whose diameter was the same as the unexpanded precursor, was similarly determined. Weight % of components was determined by thermogravimetric analysis of the expanded sintered product.

The expanded PTFE comprised interconnecting voids with the solid portion being comprised mostly of nodes and fibrils, as more fully described in U.S. Pat. No. 3,983,566. The calcium phosphate appears clustered around and in the nodes. Spaces between nodes appear to average 50-200 microns.

Volume percent voids and volume percent components were accordingly calculated and are recorded below:

| | |
|---|---|
| Bulk density of expanded sintered beading | .302 gm/cc |
| Weight % PTFE | 32.5 |
| Weight % TCP (tricalcium phosphate) | 67.5 |
| Volume % PTFE | 4.4 |
| Volume % TCP (tricalcium phosphate) | 6.8 |
| Volume % voids | 88.8 |

EXAMPLE 2

A beading prepared as in Example 1 was torn along its longitudinal axis to form two composite halves each with its interior midplane surface now exposed. The composites halves were then steam autoclaved and subsequently wet out by saline solution by immersing in the solution and manipulating to squeeze out air and suck in solution. The wet out composite was placed in a bone defect in the jaw of a canine with the newly generated, formerly midplane surface placed in apposition to the bone. It filled the defect cavity. Soft flap tissue from the gum was placed over the composite. In about three months time, histological studies show what appears to be new bone ingrowth having well vascularized areas. The remaining one-third of the defect cavity directly underlying the soft tissue had filled with fibrous tissue creating a soft cushion over the hard bone.

EXAMPLE 3

A flexible beading composite was prepared as in Example 1. It was further prepared and installed in the jaw of a canine as in Example 2 except that an expanded PTFE membrane with a 0.45 micron maximum pore size as determined by methanol bubble point method (ASTM F316-80) was placed over the composite and then soft flap tissue from the gum was placed over the composite membrane assembly. In about three months time, about 80% of the overall graft space adjacent to the parent bone filled with well vascularized new woven bone and about twenty percent further removed from the parent bone was filled with fibrous tissue.

What is claimed is:

1. A bone growth material for filling in defects or hollow portions of bones to coalesce with bone tissue wherein said bone growth matrix consists essentially of between 1.5 to 12% by volume expanded polytetrafluoroethylene having a void content of greater than 70% and comprising a matrix of interconnected channels defined by nodes and fibrils and between 2.5 to 18% by volume calcium phosphate particles interspersed throughout the expanded polytetrafluoroethylene, in which the matrix is coherent and resilient and in which the interconnected channels are of a size capable of allowing for vascularized tissue ingrowth.

2. A bone growth material as described in claim 1 wherein said calcium phosphate is calcium triphosphate of the formula $CA_5(PO_4)_3OH$.

3. A bone growth material as described in claim 1 wherein said calcium phosphate is resorbable calcium phosphate.

4. A bone growth material as described in claim 1 wherein said expanded PTFE comprises between 3 and 6 by volume percent of the matrix and said calcium phosphate comprises between 4 and 8 volume percent.

* * * * *